United States Patent [19]

Calabrese

[11] Patent Number: 4,886,052

[45] Date of Patent: Dec. 12, 1989

[54] EMERGENCY MEDICAL CERVICAL COLLAR

[75] Inventor: Anthony Calabrese, Philadelphia, Pa.

[73] Assignee: Charles Greiner and Company, Inc., Westville, N.J.

[21] Appl. No.: 125,730

[22] Filed: Nov. 30, 1987

Related U.S. Application Data

[63] Continuation-in-part of Ser. No. 70,992, Jul. 8, 1987, abandoned, which is a continuation-in-part of Ser. No. 41,898, Apr. 23, 1987, abandoned.

[51] Int. Cl.$^4$ ............................................... A61F 5/04
[52] U.S. Cl. ................................. 128/75; 128/DIG. 23
[58] Field of Search .................. 128/75, 78, 846, 87 B, 128/76 R, 84 R, DIG. 23, DIG. 15, 76 B

[56] References Cited

U.S. PATENT DOCUMENTS

| | | |
|---|---|---|
| Re. 32,219 | 8/1986 | Garth .................................. 128/76 R |
| D. 095,729 | 2/1935 | Brown . |
| 106,091 | 8/1870 | Stowe ....................................... 128/89 |
| D. 209,116 | 10/1967 | Treutelaar ............................... D83/1 |
| D. 213,742 | 4/1969 | Bond ........................................ D83/1 |
| D. 228,964 | 10/1973 | Sarnoff ................................. D83/1 K |
| D. 278,747 | 5/1985 | Peach, Jr. ............................... D24/64 |
| D. 289,085 | 3/1987 | Nesbitt ................................... D24/64 |
| 1,301,276 | 4/1919 | Kroetz . |
| 2,151,458 | 3/1939 | Allen ........................................ 128/87 |
| 2,325,300 | 7/1943 | Bisnoff .................................... 128/87 |
| 2,556,793 | 6/1951 | Brown .................................... 128/164 |
| 2,672,146 | 3/1954 | Touson .................................. 128/303 |
| 2,692,595 | 10/1954 | Blair, Jr. ................................. 128/87 |
| 2,740,399 | 4/1956 | Judovich ............................... 128/75 |
| 2,818,063 | 12/1957 | Smith et al. ............................ 128/87 |
| 2,827,896 | 3/1985 | Ward ...................................... 128/75 |
| 3,042,027 | 7/1962 | Monfardini ........................... 128/75 |
| 3,156,239 | 11/1964 | Uribe ...................................... 128/75 |
| 3,189,917 | 2/1962 | Sims ........................................ 2/3 |
| 3,313,297 | 4/1967 | Applegate et al. .................... 128/75 |
| 3,504,667 | 4/1970 | McFarlane ........................... 128/75 |
| 3,535,718 | 10/1970 | Murcott ....................... 128/DIG. 15 |
| 3,540,439 | 11/1970 | Gaylord ................................ 128/75 |
| 3,724,453 | 4/1973 | Dixon et al. ....................... 128/87 R |
| 3,756,226 | 9/1973 | Calabrese et al. .................... 128/75 |
| 3,759,256 | 9/1973 | O'Malley ............................ 128/89 A |
| 3,765,412 | 10/1973 | Ommaya et al. ....................... 128/75 |

(List continued on next page.)

OTHER PUBLICATIONS

*Orthopaedic Appliance Atlas*, p. 240, FIGS. 296, 297, 1952.

Primary Examiner—Edgar S. Burr
Assistant Examiner—Tonya Lamb
Attorney, Agent, or Firm—Panitch Schwarze Jacobs and Nadel

[57] ABSTRACT

The present invention is an emergency medical cervical collar suitable for land or water rescue operations. The collar more completely immobilizes the cervical portion of the victim's spine, and can be rapidly placed on the victim with minimal disturbance to the cervical portion of the spine. The collar includes generally U-shaped front and rear halves which are flexible, light weight, non-toxic, water resistant and buoyant in water. A flexible strap fastener is coupled to the rear collar half. Strap fastener guides are coupled to the front collar half so as to swivel thereon. Opposite end portions of the strap fastener are threaded through the strap fastener guides, and the strap fastener end portions are folded back and drawn evenly through the guides. The guides swivel as the collar halves are drawn together whereby the collar halves self-align. Each end portion of the strap fastener is provided with fastener material, and portion of the strap fastener therebetween is provided with mating fastener material so that the strap fastener end portions can be folded back and releasably attached to the portion therebetween whereby the collar halves are securely joined together as aligned. A second flexible strap fastener is coupled to the rear collar half so as to swivel thereon. The second strap fastener is looped around the person's head including the person's forehead, to prevent rotation or side-to-side movement of the head. A pad member is slideably mounted on the second strap fastener and is provided with a friction surface for engaging the person's forehead.

44 Claims, 9 Drawing Sheets

U.S. PATENT DOCUMENTS

| | | | |
|---|---|---|---|
| 3,776,244 | 12/1973 | Morgan | 128/76 B |
| 3,779,549 | 12/1973 | MacNeil | 273/1 B |
| 3,818,509 | 6/1974 | Romo et al. | 2/3 R |
| 3,819,796 | 6/1974 | Webster | 264/321 |
| 3,877,426 | 4/1975 | Nirschl | 128/DIG. 15 |
| 3,957,040 | 5/1976 | Calabrese | 128/75 |
| 4,141,368 | 2/1979 | Meyer | 128/87 B |
| 4,143,654 | 3/1979 | Sherman | 128/87 R |
| 4,161,946 | 7/1979 | Zuesse | 128/75 |
| 4,202,327 | 5/1980 | Glancy | 128/78 |
| 4,207,881 | 6/1980 | Richter | 128/89 A |
| 4,211,218 | 7/1980 | Kendrick | 128/87 R |
| 4,219,193 | 8/1980 | Newman | 272/94 |
| 4,299,209 | 11/1981 | Behrens et al. | 128/87 B |
| 4,325,363 | 4/1982 | Berkeley | 128/75 |
| 4,383,523 | 5/1983 | Schurman | 128/75 |
| 4,411,258 | 10/1983 | Pujals, Jr. | 128/60 |
| 4,502,471 | 3/1985 | Owens | 128/75 |
| 4,515,153 | 5/1985 | Calabrese | 128/75 |
| 4,538,597 | 9/1985 | Lerman | 128/75 |
| 4,543,947 | 10/1985 | Blackstone | 128/75 |
| 4,562,833 | 1/1986 | Pujals, Jr. | 128/75 |
| 4,582,051 | 4/1986 | Greene et al. | 128/76 R |
| 4,589,407 | 5/1986 | Koledin et al. | 128/87 R |
| 4,593,788 | 6/1986 | Miller | 182/3 |
| 4,594,999 | 6/1986 | Nesbitt | 128/87 |
| 4,617,691 | 10/1986 | Monti et al. | 128/DIG. 23 |
| 4,620,530 | 11/1964 | Lanier et al. | 128/75 |
| 4,628,913 | 12/1986 | Lerman | 128/78 |
| 4,643,174 | 2/1987 | Horiuchi | 128/76 R |
| 4,650,182 | 3/1987 | Ross | 272/95 |
| 4,657,003 | 4/1987 | Wirtz | 128/133 |
| 4,665,908 | 5/1987 | Calkin | 128/134 |
| 4,677,969 | 7/1987 | Calabrese | 128/75 |
| 4,708,129 | 11/1987 | Pujals, Jr. | 128/75 |
| 4,712,540 | 12/1987 | Tucker et al. | 128/76 R |

EMERGENCY MEDICAL CERVICAL COLLAR

CROSS-REFERENCE RELATED APPLICATION

This application is continuation-in-part of U.S. Ser. No. 70,992, entitled "Emergency Medical Cervical Collar", filed on July 8, 1987, now abandoned, which is a continuation-in-part of U.S. Ser. No. 041,898, entitled "Emergency Medical Cervical Collar", filed on Apr. 23, 1987, now abandoned.

BACKGROUND OF THE INVENTION

Cervical collars for use in a hospital environment are well-known. U.S. Pat. No. 3,756,226 discloses a cervical collar which may be used in such an environment. The collar comprises front and rear halves which are secured together by mating strap fasteners. The collar halves are applied to the patient's neck region to immobilize the cervical portion of the patient's spine. In use, the collar halves are manually aligned and then fastened by applying the mating strap fasteners along the side or end portions of the collar halves. The front half of the collar is provided with a chin cavity and support portion and a rigid support member to prevent the patient's head from tilting forward and causing flexion of the cervical portion of the spine. The rear collar half is provided with a rigid support member to prevent the patient's head from tilting rearwardly and causing hyperextension of the cervical portion of the spine. The collar halves overlap at each side region of the patient's neck, below the level of the ear. The front collar half embraces the patient's jawbone only at the chin region. As a result, rotation or side-to-side motion of the patient's head is not entirely prevented and the cervical portion of the patient's spine is not completely immobilized.

In the emergency medical environment, a cervical collar should be capable of being assembled rapidly and reliably to completely immobilize the cervical portion of the victim's spine so that the victim can be transported from the accident site as quickly as possible and without danger of secondary injury. A cervical collar comprising collar halves as in U.S. Pat. No. 3,756,226 requires a certain dexterity in aligning the collar halves before the halves are fastened together. If the collar halves are not properly aligned when first applied to the victim's neck region, it may be necessary to lift the victim's head a number of times to enable the rear half of the collar to be shifted into alignment with the front half. Also, although a collar of this type may adequately serve to prevent flexion and hyperextension of the cervical portion of the victim's spine, the collar does not sufficiently embrace the victim's jawbone and skull so as to entirely eliminate rotation of side-to-side movement of the victim's head. It is therefore desireable to apply a separate strap across the victim's forehead as a further precautionary measure to prevent rotation or side-to-side movement of the head and more completely immobilize the cervical portion of the spine. The victim is typically placed on an evacuation board which is provided with such a strap. If the evacuation board strap has been damaged or lost, or otherwise not provided, the cervical collar alone cannot completely immobilize the cervical portion of the spine.

The problem solved by the present invention is that of providing a cervical collar of the type disclosed in U.S. Pat. No. 3,756,226 but which is especially suited for emergency medical use, that is, a cervical collar which can be rapidly and reliably assembled at the scene of an accident (on land or in water) without having to lift the victim's head repeatedly to ensure proper alignment of the collar halves and which is capable of embracing the victim's jawbone, skull and forehead to prevent rotation or side-to-side movement of the head and thereby more completely immobilize the cervical portion of the spine so that the victim can be transported from the accident site without danger of secondary injury.

BRIEF SUMMARY OF THE INVENTION

Emergency medical cervical collar comprises first and second discrete body halves, one of the halves being a front half and the other being the rear half. Each half is generally U-shaped and preformed from a soft-flexible material. The collar is provided with means for adjustably drawing the body halves together such that the body halves self-align with the end portions of the body halves in adjustable overlapping relation, and for securely holding the body halves together as aligned.

The collar is also provided with means for adjustably encircling a portion of the victim's head including the forehead to prevent rotation or side-to-side movement of the head and thereby completely immobilizes the cervical portion of the victim's spine.

Emergency medical cervical collar which can accommodate varying neck circumferences. The collar comprises first and second discrete body halves, one of the halves being an expandable front half and the other being a rear half. Each half is generally U-shaped and preformed from a soft, flexible material. In one embodiment, the collar comprises a front half having an opening for providing access to the wearer's trachea, and a slit extending from the opening to the bottom edge of the collar half whereby the collar half is expandable to accommodate a wide range of neck circumferences including unusually large neck circumferences such as 23 inches. In another embodiment, the collar comprises a rear half having a rigid support member and slits located on opposite sides of the support member to increase the flexibility of the collar half whereby the collar half is collapsible to accommodate a wide range of neck circumferences including unusually small neck circumferences such as 11 inches.

BRIEF DESCSRIPTION OF THE DRAWINGS

For the purpose of illustrating the invention, there is shown in the drawings embodiments which are presently preferred; it being understood, however, that this invention is not limited to the precise arrangement and instrumentalities shown.

DETAILED DESCRIPTION OF THE INVENTION

Figures 1, 2:
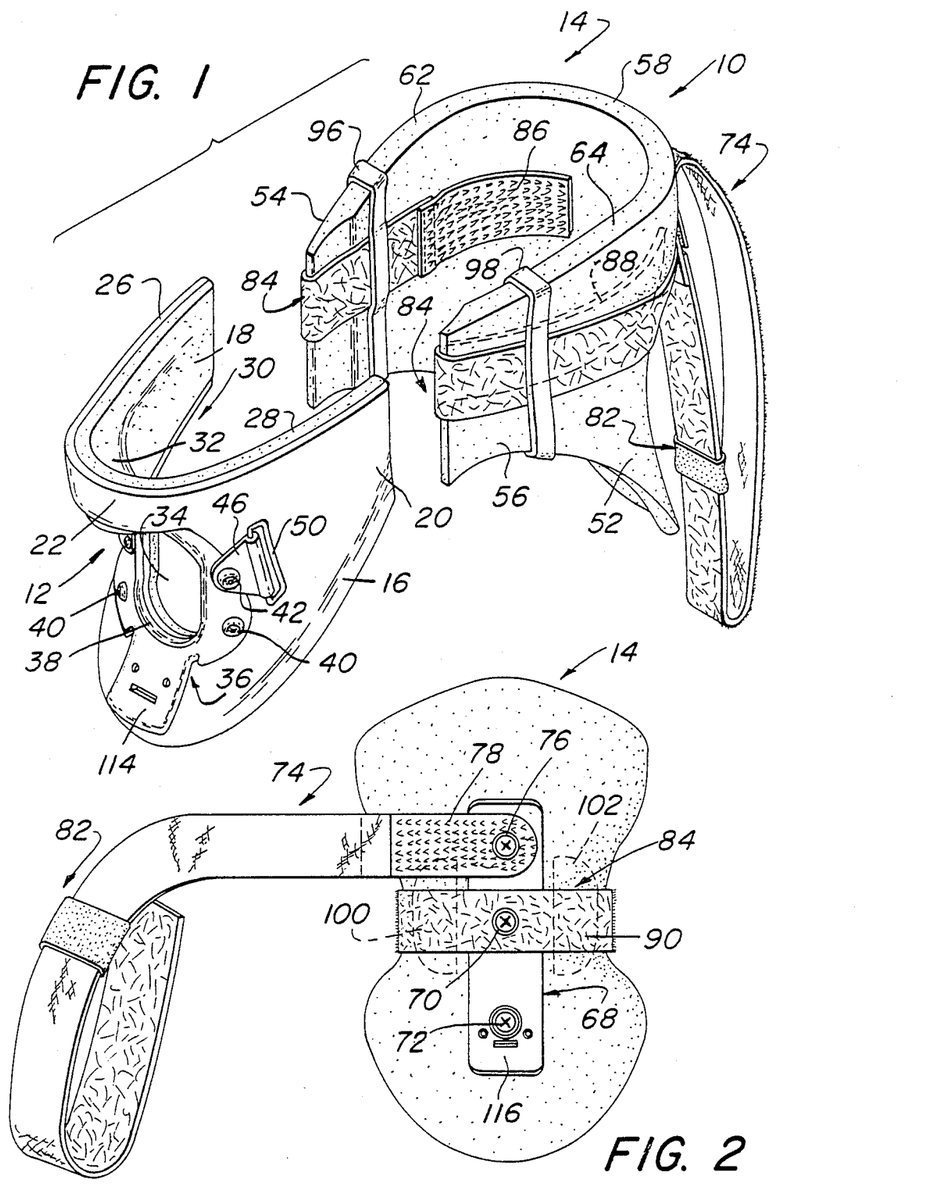
FIG. 1 is a perspective of a emergency medical cervical collar disposed in copending application Ser. No. 041,498 wherein the collar halves are separated.
FIG. 2 is a rear view of the rear collar half.

Referring to the drawings, wherein like numerals indicate like elements, there is shown in FIG. 1 an emergency medical cervical collar 10 as disclosed in copending application Ser. No. 041,898. The collar 10 includes first and second discrete body halves, one of the halves being a front half 12 for application to the front of a person's neck region and the other being a rear half 14 for application to the rear of a person's neck region.

The front half 12 comprises a generally U-shaped body 16 having end portions 18 and 20 extending from the bight portion 22. The body is preferably made from a soft, flexible, lightweight, material which is non-toxic, water resistant and buoyant in water, for example a closed cell polymeric plastic material such as polyethylene or polyurethane as disclosed in U.S. Pat. No. 3,756,226. The material of body 16 is capable of being formed in a die or mold as described in U.S. Pat. No. 3,756,226. The body may also be a reinforced laminate of the same soft material with a thinner outer layer of relatively rigid polymeric plastic material such as polyethylene (shown but not numbered in FIG. 1). The top edges 26, 28 of the front half end portions 18, 20 extend from the bight portion 22 so that the upper regions of end portions 18, 20 embrace the patient's jawbone when the collar is in place. See FIGS. 5 and 6. The upper end of the bight portion 22 is shaped to provide a chin cavity and chin support 30. A covering 32 from a material such as moleskin is adhesively or otherwise secured on the inner surface of the chin support.

The front half 12 is provided with an opening 34 at the bight portion, below the level of the chin support. The opening provides access to the tracheal region of the person's neck to enable an emergency tracheotomy to be performed at the accident scene if necessary as described in U.S. Pat. No. 4,677,969.

The opening also provides ventilation at the neck region. The front half 12 is also provided with a rigid reinforcing support member 36 at bight portion 22. Support member 36 may be made from a polymeric plastic material such as polystyrene and has an opening 38 which is aligned with opening 34 so as to provide access to the person's trachea.

The support member 36 is secured to the front half 12 by plastic rivets 40, 42. The support member 36 is generally arcuate so as to conform to the arcuate surface of front half 12 at bight portion 22. The rivets 42 also couple strap fastener guides 44, 46 to support member 36. The guides 44, 46 are made of a polymeric plastic material and are mounted on the support member 36 so as to be rotatable about the axis of each rivet 42.

Each strap fastener guide 44, 46 is preferably preformed from a single piece of material folded over so as to hold one leg of a loop 48 (50) of like material such that the loop is free to swivel about an axis coincident with the loop leg.

Figure 3:
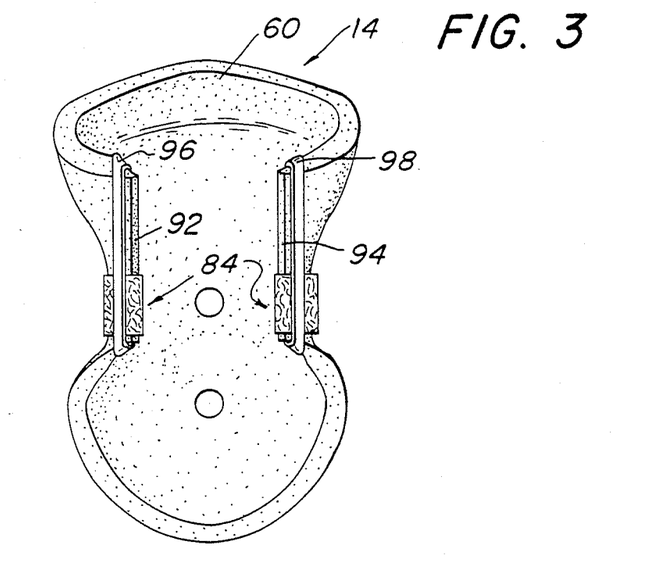
FIG. 3 is a front view of the rear collar half.

The rear half 14 comprises a generally U-shaped body 52 made from the same soft material as the material used for body 16. The body may also be a reinforced laminate of the same soft material with a thinner outer layer of relatively rigid polymeric plastic material such as polyethylene (not shown). The end portions 54 and 56 of body 52 extend from a bight portion 58. The upper end of the bight portion is shaped to provide a skull cavity and support 60 for the bottom portion of the person's skull. The top edges 62, 64 of end portions 54, 56 extend from the upper end of the bight portion 58 such that the end portions embrace the person's ears, thereby preventing the end portions 18, 20 of front half 12 from riding under the person's ear lobes or from biting a portion of either ear. Thus, the end portions 54, 56 of rear half 14 provide a protective cushion for the person's ears.

A rigid support member 68, made from the same material as member 36, is secured to the bight portion 58 of body 52 on the outer surface thereof. Support member 68 is secured to the bight portion of body 52 by plastic rivets 70, 72. Support member 68 has a curved upper portion which matches the curvature of the back portion of the person's neck near the base of the skull. The curved portion extends to the region of the skull support 60. A flexible strap fastener 74 is coupled to the curved upper portion of support member 68 by a plastic rivet 76. Rivet 76 does not secure member 68 to the body 52. Preferably, the rivet is located entirely outside the body 52 so as not to impinge on the back region of the person's skull. The strap fastener 74 is coupled along an end portion 78 thereof to support member 68 so that the strap fastener can be moved or swiveled about the axis of rivet 76.

The outer face of strap fastener 74 at end portion 78 thereof is provided with a fastener material such as VELCRO brand fastener materials. The opposite face of the strap fastener 74, including the opposite end portion 80, is provided with mating fastener material, also VELCRO brand fastener materials. Prior to use, strap fastener 74 is formed in a loop with the end portions 78, 80 releasably interlocked. In use, end portions 78, 80 are separated, the strap fastener is looped around the person's forehead, and the end portions 78, 80 are reattached. Strap fastener 74 is mounted on member 68 along the curved upper portion thereof so as to ensure that the strap fastener is applied evenly across the person's forehead. Thus, a person's forehead will be pitched in the same direction as the curved portion of member 68. The length of strap fastener 74 is chosen to accommodate a wide range of head sizes. A pad 82 in the form of a loop of material such as rubber or horsehide is applied to the strap fastener 74 so as to be slidable therealong. The outer surface of pad 82 provides a friction surface for contacting the person's forehead thereby preventing the strap fastener 74 from sliding on the person's forehead. The pad also serves as a cushion which prevents the strap fastener from biting the person's forehead.

Figure 4:
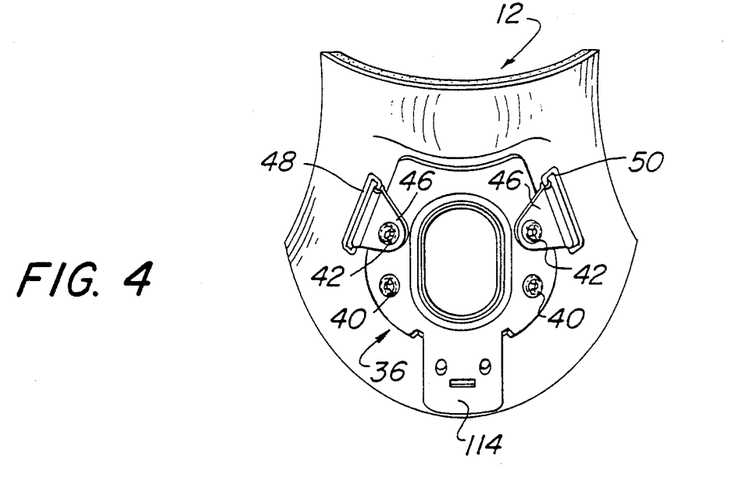
FIG. 4 is a front view of the front collar half.

A second flexible strap fastener 84 is coupled along a medial portion thereof to member 68 by rivet 70. The outer face of strap fastener 84 is provided with fastener material, such as Velcro, along opposite end portions 86, 88. The same face of the strap fastener is provided with mating fastener material, also VELCRO, along portion 90 between end portions 86, 88. The strap fastener 84, in cooperation with the strap fastener guides 44, 46, is used to align front half 12 and rear half 14 and to draw and secure the front and rear halves together. The length of the strap fastener 84 is chosen to accommodate a wide range of head and neck sizes.

Prior to use, strap fastener 84 is wrapped around a central, generally convex portion of the outer surface of body 52, around end edges 92, 94, and along the inside surface of the body 52. The strap fastener 84 is held in position by paper bands 96, 98 which are wound around or slipped over each end portion of body 52. When the collar is used, the paper bands are first torn away so as to free the strap fastener 84 as further described below.

If desired, D-shaped openings 100, 102, as shown in phantom, may be formed in the rear collar half 14 on either side of the support member 68. Openings 100, 102 permit the rear half 14 to flex to a substantially flat position so as to facilitate use while providing ventilation in use.

Figure 9:
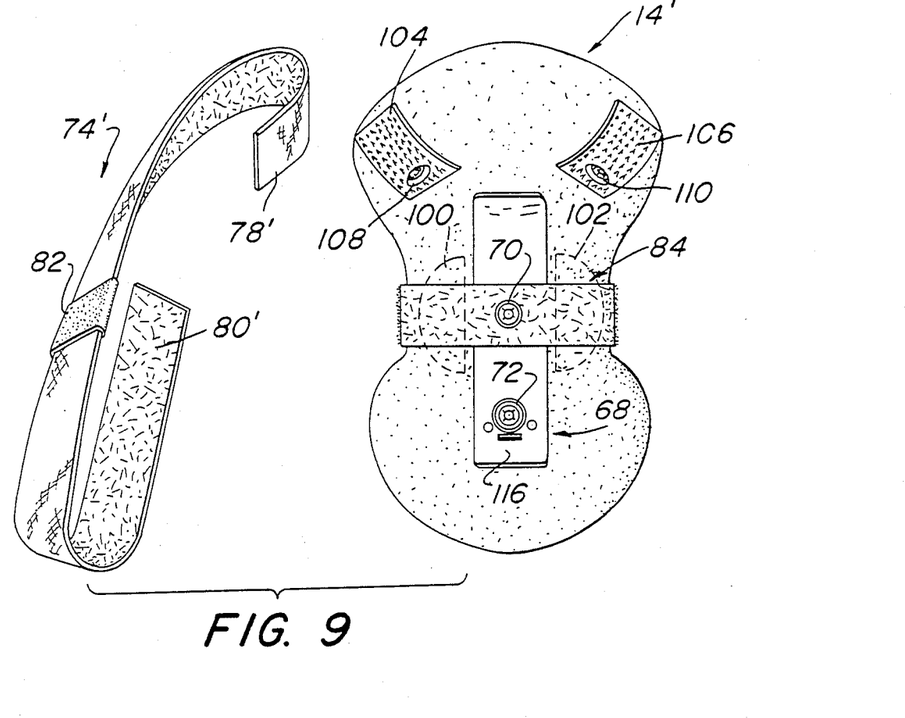
FIG. 9 shows an alternate embodiment of the rear collar half and the strap fastener for application to the person's forehead.
Figure 10:
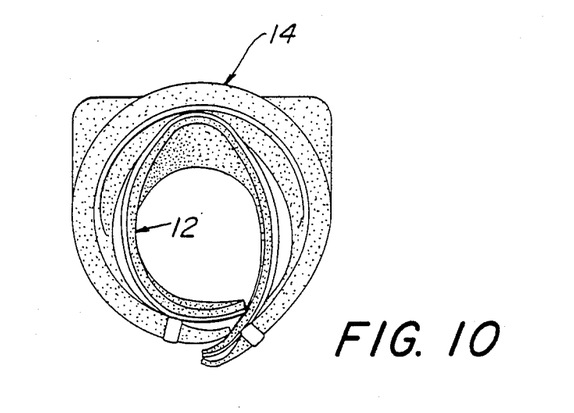
FIG. 10 shows the collar halves separated and rolled, one over the other, to form a compact tubular shaped unit for the purpose of storage.

In an alternative embodiment of the rear collar half 14' and strap fastener 74' as shown in FIG. 9, rivet 76 may be dispensed with, and the strap fastener 74' may be coupled to the rear collar half 14' by swatches 104, 106 of VELCRO brand fastener materials fastener material. Each swatch 104, 106 is secured to the body 52, on either side of support member 68, by plastic rivets 108, 110. Strap fastener 74' is provided with mating VELCRO brand fastener materials fastener material along a face thereof so that opposite end portions 78', 80' of the strap fastener may be secured to the swatches 104, 106 by a releasable interlock. The rear collar half 14' is otherwise identical to rear collar half 14.

Figure 11:
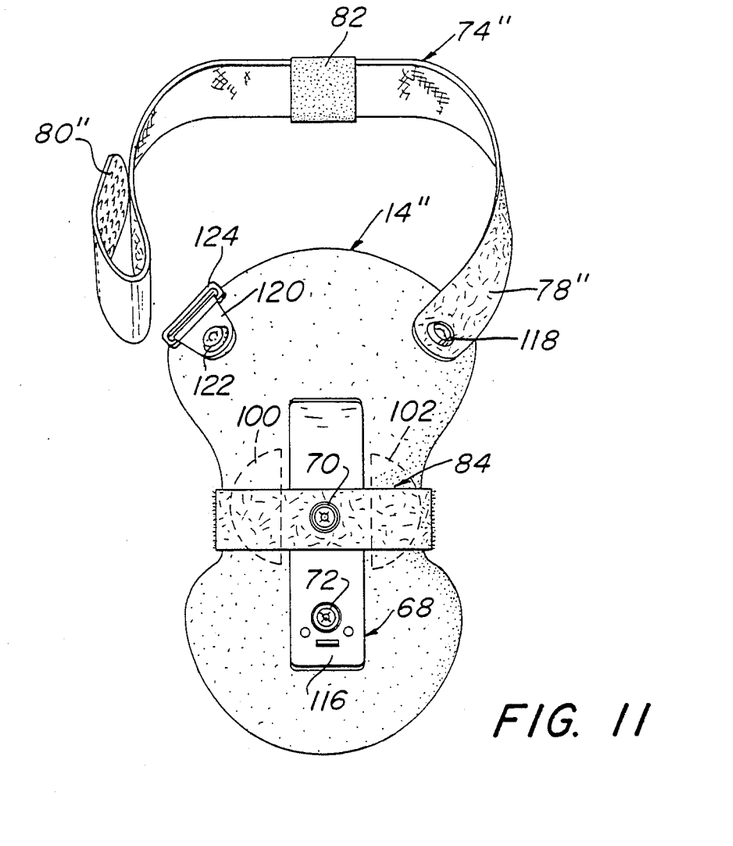
FIG. 11 shows a further embodiment of the rear collar half and the strap fastener for application to the person's forehead.

In a further embodiment of the rear collar half 14" and strap fastener 74" as shown in FIG. 11, the rivet 76 is dispensed with, and the strap fastener 74" is coupled at end portion 78" to rear collar half 14" by a plastic rivet 118 at one side of the rear collar half bight portion. The strap fastener 74" can be moved or swiveled about the axis of rivet 118. The outer face of the strap fastener 74" including end portion 78" is provided with fastener material such as VELCRO brand fastener materials. The opposite end portion 80" of the strap fastener, along the same face, is provided with mating fastener material such as VELCRO brand fastener materials. Prior to use, strap fastener 74" is formed in a loop with end portions 78", 80" releasably interlocked. A strap fastener guide 120, identical to guides 44, 46, is coupled by a plastic rivet 122 to the rear collar half at another side of the rear collar bight. The strap fastener guide 120 is rotatable about the axis of rivet 122. Strap fastener guide 120 holds one leg of a guide loop 124, identical to guide loops 48, 50, such that the loop is free to swivel about an axis coincident with the loop leg. The rear collar half 14" is otherwise identical to rear collar half 14.

The end portions 18, 20 of front collar half 12 extend from the bight portion 22 a substantially greater distance than end portions of the front collar half disclosed in U.S. Pat. No. 3,756,226. Similarly, end portions 54, 56 of rear collar half 14 extend a substantially greater distance from bight portion 58 than end portions of the rear collar half disclosed in U.S. Pat. No. 3,756,226. The distance over which the end portions of each collar half 12, 14 extend is chosen to provide a wide range of overlap between the end portions so as to accommodate a wide range of head and neck sizes.

The approach previously taken was to provide collar halves having at least three different sizes as determined by the length of the end portions of the collar half measured from the bight portion. In the present invention, one pair of front and rear collar halves 12, 14, each having end portions which extend over a substantially greater distance from the bight portion, suffices to accommodate most adult head and neck sizes. Another pair of collar halves 12, 14, each having end portions which extend over a substantially greater distance from the bight portion, suffices to accommodate most children's head and neck sizes. Thus, only two sizes of collars are required to treat almost all ages and neck sizes. A single adult size collar 10 may have end portions which extend from the collar half bight portions so as to accommodate neck sizes between approximately 11 and 18 inches which is believed to be a suitable range for most adults. A single periatric size collar 10 may have end portions which extend from the collar half bight portions so as to accommodate neck sizes between approximately 5 and 10 inches which is believed to be a suitable range for most children between approximately 3 years and 13 years of age.

In an emergency medical situation involving injury to the cervical portion of the victim's spine, the cervical portion of the spine should be rapidly and completely immobilized with minimal disturbance to the victim. In applying the cervical collar as disclosed herein in an emergency medical situation, strap fastener 74 remains looped back on itself and is swiveled to the cleared position, away from and to the side of the rear collar half so as to avoid entanglement with strap fastener 84 and so as to render strap fastener 74 available for immediate access and use, as described more fully below, after the collar halves 12, 14 have been coupled together. The rear collar half 14 is flattened, with paper bands 96, 98 in place, and then slipped behind the victim's neck. Paper bands 96, 98 are then broken and discarded to free strap fastener 84 from rear collar half 14. Front collar half 12 is then applied to the victim's front neck portion with chin support 30 immediately beneath the victim's chin and end portions 18, 20 extending around and embracing the sides of the victim's jawbone and neck. The rear collar half end portions 54, 56 lie inside front collar half end portions 18, 20.

Figure 5:
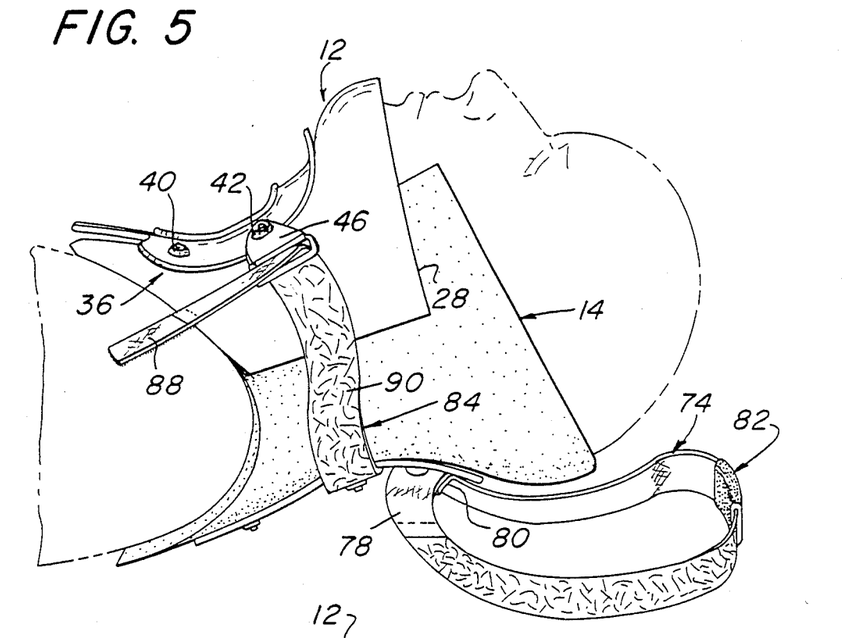
FIG. 5 shows the collar halves being drawn together in actual use.

End portions 86, 88 of strap fastener 84 are then threaded through the strap fastener guide loops 48, 50. These loops may first be swiveled on guides 44, 46, away from the outer surface of front collar half body 16, so as to facilitate threading of the strap fastener end portions 86, 88 therethrough. The strap fastener end portions 86, 88 are then folded back and pulled evenly so as to draw them by equal lengths through the strap fastener guide loops 48, 50 thereby drawing collar halves 12, 14 together as shown in FIG. 5. The strap fastener guides 44, 46 rotate or swivel on the rivets 42 so that the front and rear collar halves 12, 14 self-align as they are being drawn together. The strap fastener guide loops 48, 50 swivel on guides 44, 46 towards a closed position as the strap fastener end portions 86, 88 are pulled to draw the collar halves 12, 14 together. The strap fastener end portions 86, 88 are then secured in a releasable interlock to strap fastener portion 90.

Figure 6:
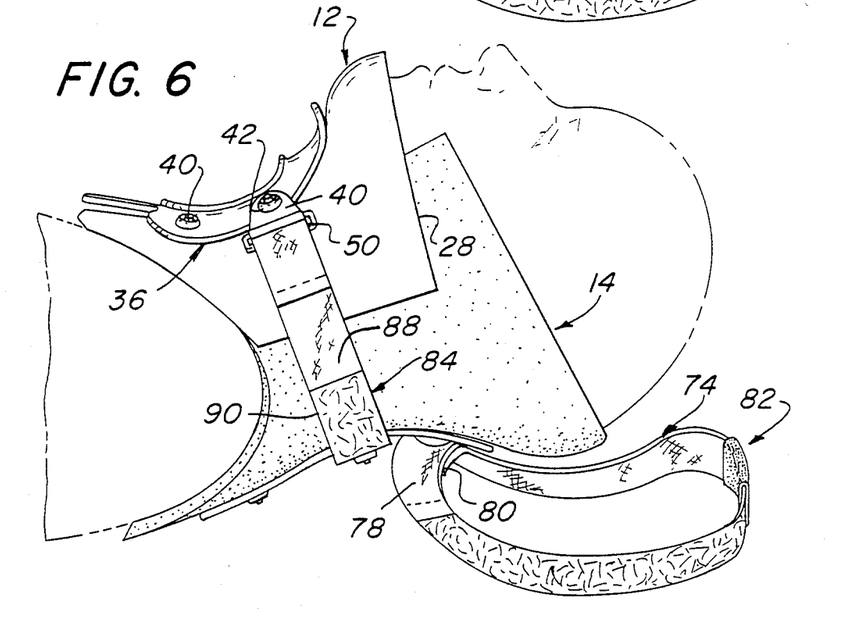
FIG. 6 shows the collar halves drawn together, aligned and fastened in place.

The joined collar halves 12, 14 securely embrace the victim's head region to more completely immobilize the cervical portion of the spine as shown in FIG. 6. The top edges 26, 28 of front collar half end portions 18, 20 extend above the victim's jaw bone so that the front collar end portions embrace substantially all of the person's jaw bone, and the rear collar half end portions 54, 56 extend over the victim's ear thereby providing a cushioned ear guard while embracing substantial portions of the sides of the victim's skull whereby the assembled collar prevents rotation or side-to-side motion of the victim's head. Thus, the assembled emergency medical cervical collar prevents flexion and hyperextension of the cervical portion of the victim's spine as well as rotation or side-to-side motion of the victim's head.

Figure 7:
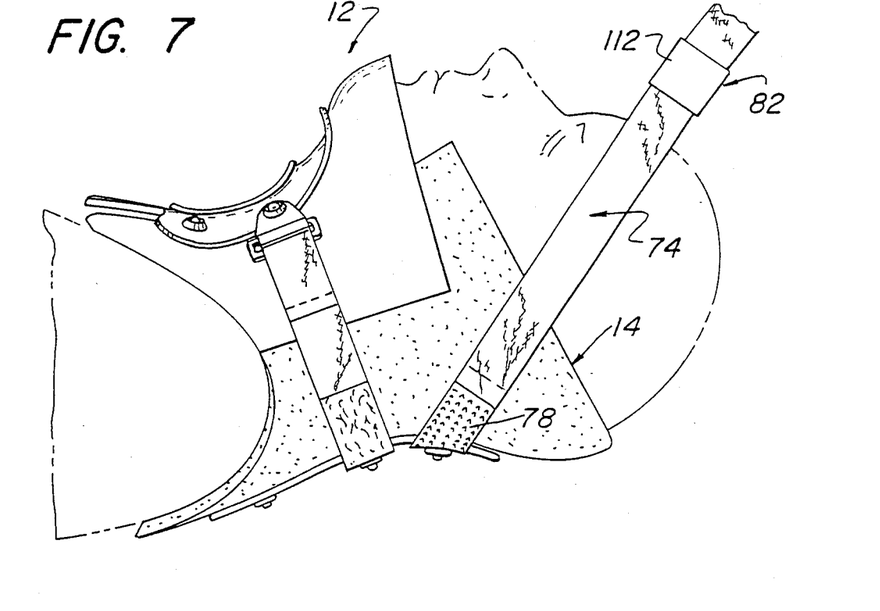
FIG. 7 shows the collar halves aligned and fastened in place with a strap fastener being applied to the victim's forehead.
Figure 8:
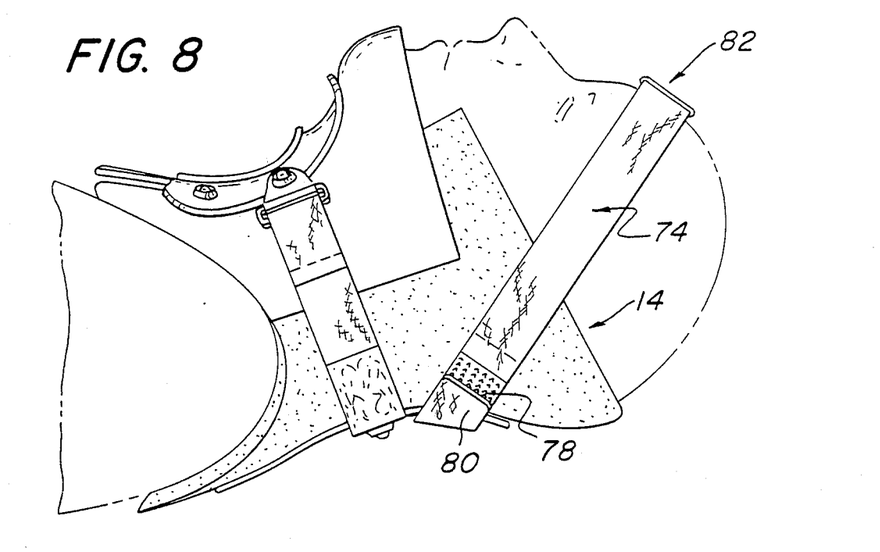
FIG. 8 shows the strap fastener applied to the victim's forehead and secured in place.

To further immobilize the cervical portion of the spine, strap fastener 74 is then wrapped around the victim's head so as to traverse the forehead as shown in FIG. 7. The strap fastener end portion 80 is first separated from end portion 78 and the strap fastener is then looped around the victim's head, traversing the victim's forehead. Pad 82 is positioned along the strap fastener so as to locate at a central region of the forehead as shown in FIG. 8. The pad serves as a cushion and also prevents the strap fastener from sliding on the victim's forehead. The strap fastener end portion 80 is then secured in a releasable interlock to end portion 78.

The cervical portion of the victim's spine is thus more completely immobilized in a rapid and efficient manner with minimal disturbance to the victim, all of which are extremely important in an emergency medical situation. It is also unnecessary to apply the evacuation board strap to the victim's forehead to prevent rotation or side-to-side movement of the victim's head. However, should the attending medic wish to use the evacuation board strap as well, the strap (not shown) may be applied across the outer friction surface 112 of pad 82. The outer surface of the pad holds the evacuation board strap in position across the victim's forehead.

Virtually the same procedure is used to assemble the alternative embodiments of the emergency medical cervical collar shown in FIGS. 9 and 11. In using the alternative embodiment of the collar shown in FIG. 9, the strap fastener 74' is secured at one end to one of the swatches of fastener material 104, 106 before the rear collar half 14' is applied to the back region of the victim's neck. The strap fastener 74' is extended to the cleared position before the rear collar half 14' is slipped behind the victim's head. Thereafter, the same steps are followed to draw, align and couple the collar halves 12, 14' together. The strap fastener 74' is then looped around the victim's head so as to traverse the forehead, and the free end portion of the strap fastener is then secured in a releasable interlock to the other swatch of fastener material.

In using the alternative embodiment of the collar shown in FIG. 11, the strap fastener 74" is looped back on itself and is swiveled to the cleared position before the rear collar half 14" is slipped behind the victim's head. Thereafter, the same steps are followed to draw, align and couple the collar halves 12, 14" together. The strap fastener end portions 78", 80" are then separated and the strap fastener is then looped around the victim's head so as to traverse the forehead. The free end portion of the strap fastener is drawn through guide loop 124, folded back and pulled so as to draw the strap fastener taut. As the strap fastener is being pulled taut, the guide 120 rotates or swivels on rivet 122 to align properly with the strap fastener. The strap fastener material at end portion 80" is then secured in a releasable interlock to the mating fastener material on the same face of the strap fastener.

In all embodiments of the rear collar half 14, 14', 14" and strap fastener 74, 74', 74", the strap fastener secures the victim's head against rotation or side-to-side movement. Thus, the strap fastener overlaps the collar halves along the victim's ear region thereby securing the collar end portions against the sides of the victim's head while also overlapping and securing the victim's forehead.

The emergency medical cervical collar 10 is believed to significantly advance the art by providing a cervical collar which can be rapidly assembled with the collar halves properly aligned and with minimal disturbance to the victim. The collar 10 more completely immobilizes the cervical portion of the victim's spine, preventing flexion, hyperextension and rotation of side-to-side movement of the victim's head whereby the victim can be safely transported from the accident scene to the hospital for further treatment.

It should be appreciated that if each collar half is reinforced with a thin rigid outer layer of polyethylene, as previously mentioned, the support members 36, 68 may be dispensed with. The strap fastener guides 44, 46 (FIG. 4) and 120 (FIG. 11) may then be coupled directly to the collar half bodies, and the strap fasteners 74, 84 (FIG. 2) may be coupled directly to the rear collar half body.

In each embodiment disclosed herein, the front collar half support member 36 may be provided with a tab structure 114 (FIG. 4) and the rear collar half support member 68 may be provided with a like tab structure 116 (FIG. 2) to accommodate a cervical stabilizer (not shown) as described in U.S. Pat. No. 4,515,153. The cervical stabilizer can be applied to the victim at the hospital site.

The material composition of the emergency medical cervical collar 10 allows the collar to be used efficiently in water rescue operations. Since the body portions of each collar half are water resistant and buoyant, the collar halves may be placed at ready, floating near the victim, while the medic holds and orients the victim. The rear collar half can then be withdrawn from the water and placed behind the victim's neck region to help buoy the victim's neck thereby helping to stabilize the cervical portion of the victim's spine and facilitating application of the front collar half. The collar may then be quickly assembled as previously described with minimal disturbance to the victim while the victim remains in water.

The material composition of the emergency medical cervical collar 10 also allows the victim to be X-rayed with the collar assembled in place on the victim. Thus, the collar 10 need not be disassembled and removed to enable X-rays to be taken whereby the cervical portion of the victim's spine can remain immobilized without further disturbance to the victim during the X-ray procedure.

Figures 12, 13:
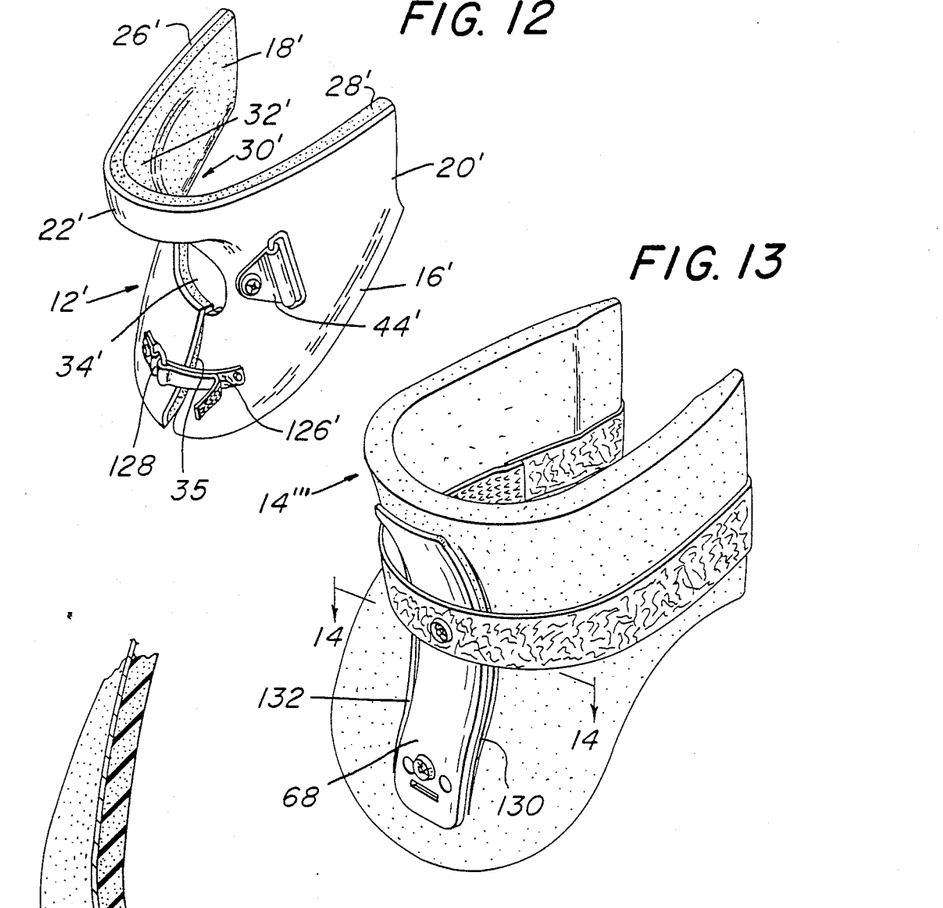
FIG. 12 shows a front collar half according to the present invention which accommodates persons having large neck circumferences.
FIG. 13 shows a rear half according to the present invention which accommodate persons having small neck circumferences.
Figure 14:
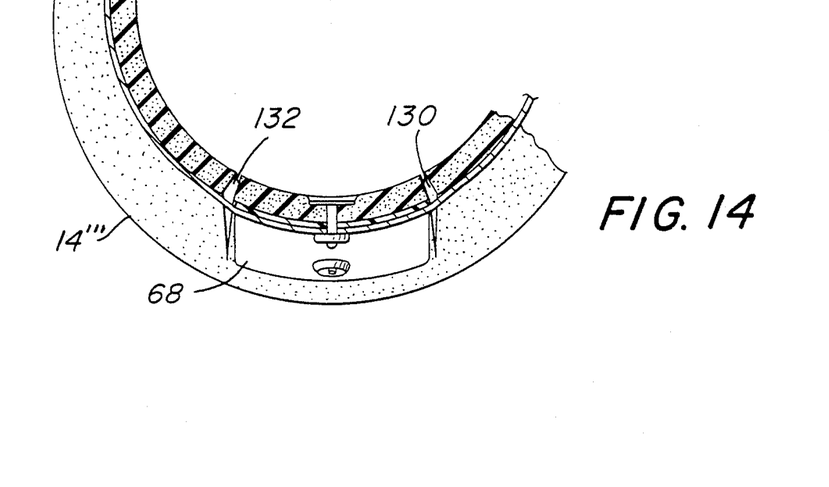
FIG. 14 is a plan view of the rear collar half taken along 14—14 of FIG. 13.

Referring to FIGS. 12 through 14, a front collar half 12' and rear collar half 14''' are disclosed according to the present invention. The front collar 12' is specifically directed to the accommodation of patients with unusually stout necks (as large as approximately 23 inch circumference). The rear collar half 14''' is specifically directed to the accommodation of patients with unusually thin necks (as small as approximately 11 inch circumference).

Referring to FIG. 12, front collar half 12' comprises a generally U-shaped body 16' having end portions 18' and 20' extending from bight portion 22'. The body is preferably made from the same soft, flexible, lightweight, non-toxic, water resistant and buoyant material as those disclosed previously. The body is provided with a reinforcing laminate of a relatively rigid polymeric plastic material such as polyethylene to provide rigidity for the collar. The top edges 26', 28' of end portions 18', 20' extend from bight portion 22' so that the upper regions of the end portions 18', 20' embrace the patient's jawbone when the collar is in place. The upper end of the bight portion 22' is shaped to provide a chin cavity and chin support 30'. A covering 32' from a material such as moleskin is adhesively or otherwise secured on the inner surface of the chin support.

Front collar half 12' is provided with an opening 34' at the bight portion, below the level of the chin support. The opening provides access to the tracheal region of the person's neck to enable an emergency tracheotomy to be performed at the accident scene if necessary as described in U.S. Pat. No. 4,677,969.

The opening also provides ventilation at the neck region. A slit 35 extends from opening 34' to the bottom edge of the collar half. The slit 35 enables the collar half to expand radially, so as to accommodate a wide range of large neck circumferences such as 23 inches. The collar half can accommodate neck circumferences ranging from 17 to 23 inches. A strap fastener 126 and guide 128 are attached to the bight portion of the collar half on opposites sides of slit 35. The strap fastener 126 has mating VELCRO brand fastener materials fastener portions on one side thereof. The strap fastener is threaded through guide 128 and folded back on itself to secure the collar half at the region of slit 35. This prevents further expansion of slit 35, and firmly secures front collar half 12' to the contour of the patient's neck region. Those skilled in the art will clearly recognize that any suitable fastening means such as an adjustable buckle, snaps or the like, can be utilized to perform the same function.

Referring to FIGS. 13 and 14, the rear collar half 14''' comprises a U-shaped body 52 as already disclosed with respect to rear collar halves 14, 14' and 14''. Rear collar half 14''' is provided with two slits 130, 132 on opposite sides of the rigid support member 68. The slits operate as partial hinges, which make the rear collar half 14''' more pliable and flexible, and enable the rear collar half to be fitted securely on patients with a small neck circumference such as 11 inches. However, the rear collar half can accommodate neck circumferences ranging from 11 to 23 inches.

Figures 15, 16, 17:
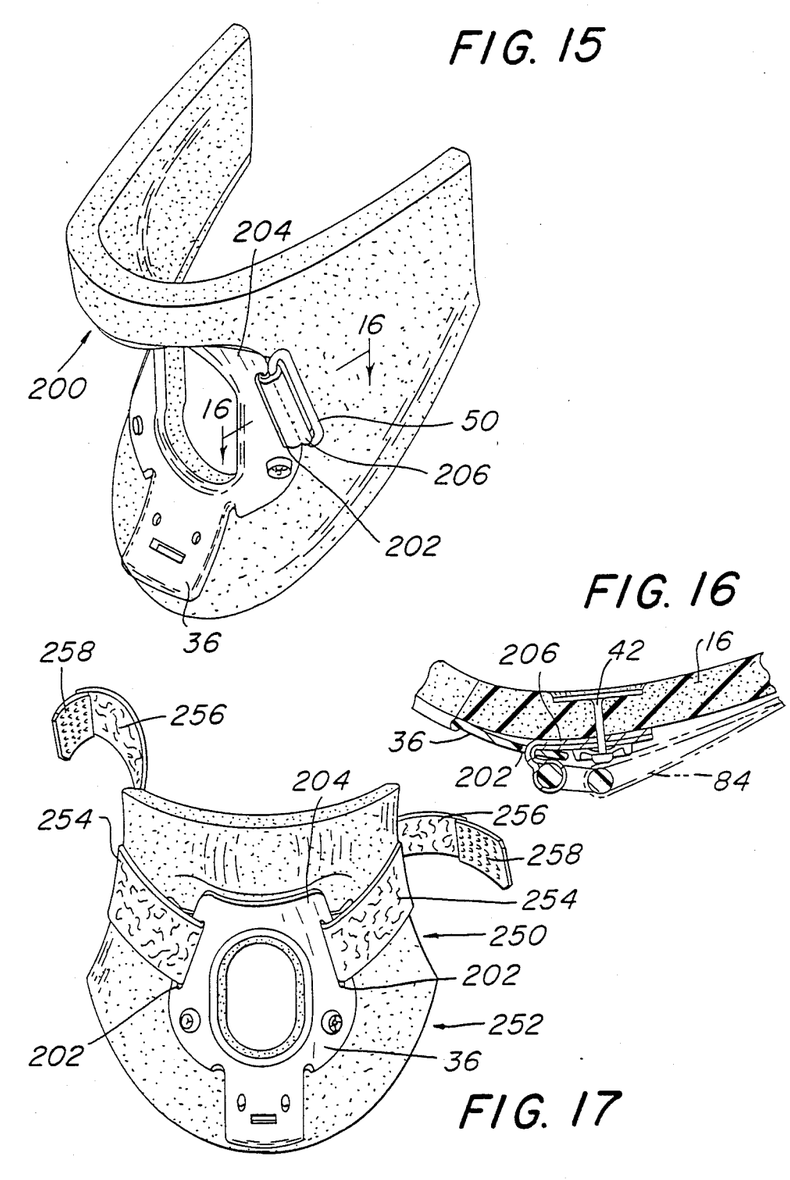
FIG. 15 is an isometric view of an alternate embodiment of the front collar half of the present invention.
FIG. 16 is a sectional view taken along lines 16—16 of FIG. 15.
FIG. 17 is an elevational view of another alternate embodiment of the front collar half of the present invention.

Referring to FIGS. 15 and 16, an alternate embodiment 200 of the front collar half is illustrated. Front half 200 is substantially the same as front half 12 illustrated in FIGS. 1, 4 and 5-8 except as noted below. Rigid reinforcing support member 36 is provided with an elongated slot 202 located along each lateral edge portion 204 of member 36 (only one shown). A strap fastener guide 206 having a loop 50 is anchored to body 16, i.e. via plastic rivet 42, and passes through slot 202 whereby a strap 84 (in phantom in FIG. 16) is passed through loop 50 as described above.

Figures 18, 19, 20:
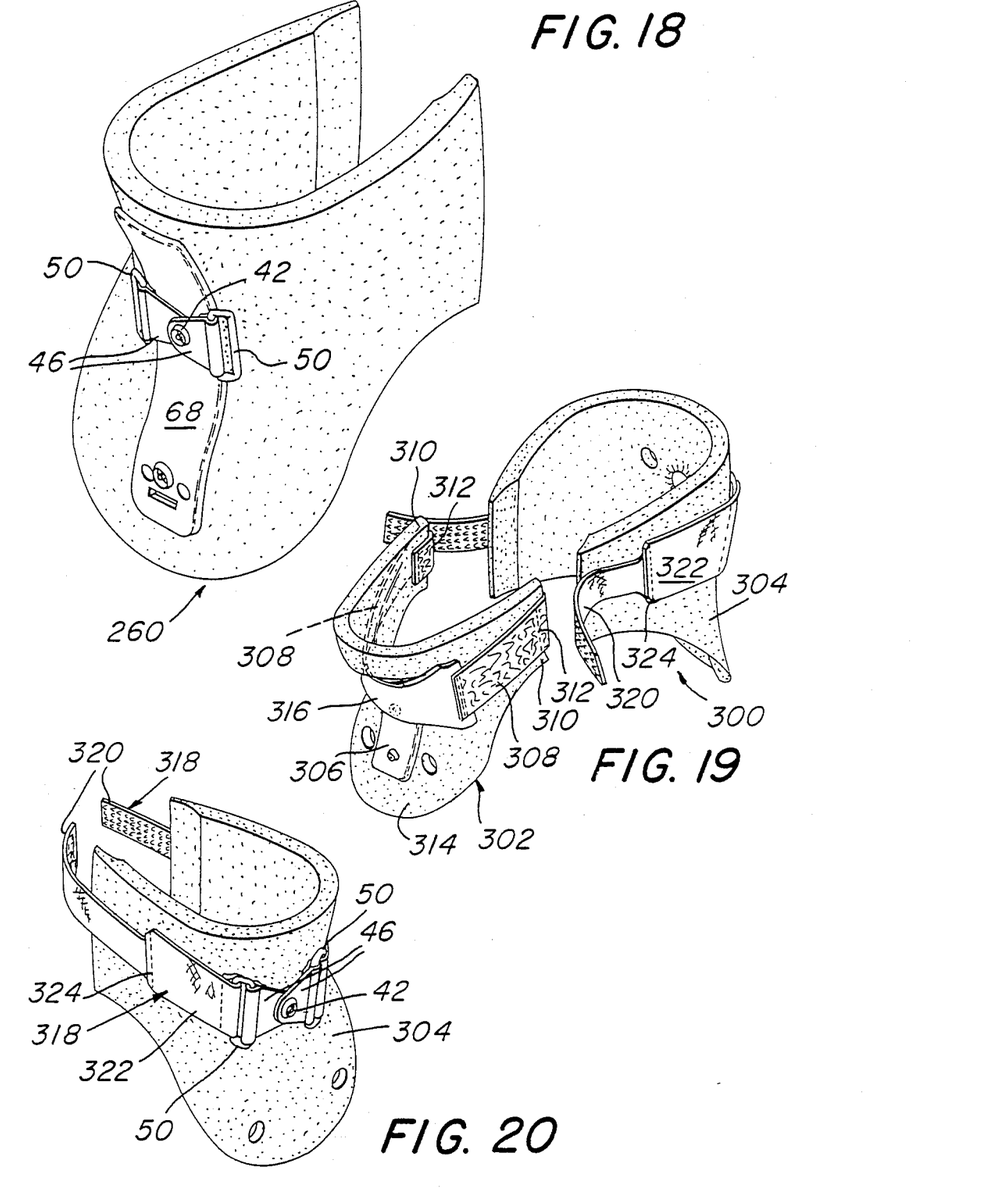
FIG. 18 is an isometric view of an alternate embodiment of the rear collar half of the present invention and is preferably used with the front collar half illustrated in FIG. 17.
FIG. 19 is an isometric view of an alternate embodiment of the present invention.
FIG. 20 is an isometric view of the rear collar half illustrated in FIG. 19.

Referring to FIGS. 17 and 18, an alternate embodiment 250 of the collar is illustrated. Collar 250 is substantially as described above except as noted below. Front collar half 252 has a rigid reinforcement support member 36, as described above with regard to front half 200. Member 36 is provided with elongated slot 202 which is located along each lateral edge portion 204 of member 36. A strap fastener 254 having VELCRO ® loops 256 and hooks 258 is anchored through each slot 202 in a conventional manner. The rear collar half 260 (See FIG. 18) includes a rigid support member 68 which is secured thereon as described above. A pair of strap fasteners guides 46 are anchored to member 68 via a fastener, such as plastic rivet 42. Each strap fastener guide 46 includes a loop 50. Each strap fastener 254 anchored to front collar half 252 is passed through its corresponding loop 50 and then secured to itself as described above.

Referring to FIGS. 19 and 20, an alternate embodiment 300, a pediatric collar, of the present invention is illustrated. The front collar half 302 and rear collar half 304 are substantially as disclosed above except as noted below, and are smaller than those collars used for adults. Front half 302 includes a rigid support member 306 secured thereto as described above. Member 306 does not have a tracheotomy opening as described above, but can be modified to include one. VELCRO ® loop fasteners straps 308 are secured to the front half 302 adjacent the free end 310 of front half 302 in a conventional manner, such as by stitching 312. Straps 308 lie against the front half 302 and are joined together across the bight 314 of half 302 by a non-elastic, plastic coated cloth material 316 shaped as a bow tie.

The rear collar half 304 does not have a rigid reinforcement member; such as not needed in pediatric applications because a child's head weighs only a few pounds and the foam material has sufficient strength to support that weight. Strap fastener guides 46 are anchored directly onto rear collar half 304 via a fastener, such as plastic rivet 42. Each guide has a loop 50. A strap 318 is anchored to each loop 50 and has a VELCRO ® hook portion 320 affixed to a non-elastic, plastic coated cloth material portion 322 in a conventional manner, such as by stitching 324. Hook portion 320 overlaps and is secured to strap 308 as described above by securing the front and rear halves together.

The present invention may be embodied in other specific forms without departing from the spirit or essential attributes thereof and, accordingly, reference should be made to the appended claims, rather than to the foregoing specification, as indicating the scope of the invention.

I claim:

1. Emergency medical cervical collar, comprising:
first and second discrete body halves, one of said halves being a front half and the other being a rear half, each half being generally U-shaped with a bight portion and a pair of end portions extending from the bight portion and preformed from soft, flexible material, said rear half having a rigid support member at the bight portion thereof and slits located in the soft flexible material on opposite sides of said support member, the slits extending along sides of said support member to increase the flexibility of said rear half, and means for securing said body halves together with the end portions of said body halves in adjustable overlapping relation.

2. Emergency medical cervical collar according to claim 1, wherein said slits constitute hinge means for permitting said rear half to flex inwardly and outwardly so as to accommodate a neck having a circumference of between approximately 11 and 23 inches.

3. Emergency medical cervical collar comprising:
first and second discrete body halves, one of said halves being a front half and the other being a rear half, each half being generally U-shaped with a bight portion and a pair of end portions extending from the bight portion, and preformed from soft flexible material, said front collar half having a chin support portion, the end portions of said front collar half extending from the chin support portion so as to enclose a substantial portion of the person's jawbone, said rear collar half having a skull portion, the end portions of said rear collar half extending unitarily from said skull portion sufficiently so as to overlap at least a portion of the person's ear, and means for securing said body halves together with the end portions of said body halves in adjustable overlapping relation, and including a rigid reinforcement support member affixed adjacent the bight portion of the front collar half and strap means affixed to said front collar half and surrounding an exterior surface of said front collar half, whereby said collar substantially prevents flexion, hyperextension and side-to-side movement of the person's head.

4. Emergency medical cervical collar according to claim 3 wherein said collar further comprises:
a pair of strap fasteners guides affixed to said rear collar half; and
strap means secured to each strap fastener guides, whereby said last-mentioned means overlies and is secured to said first mentioned strap means.

5. Emergency medical cervical collar, comprising:
first and second discrete body halves,
one of said halves being a front half and the other being a rear half, each half being generally U-shaped with a bight portion and a pair of end portions extending from the bight portion and preformed from soft, flexible material,
said front half having slit means at the bight portion thereof extending to a bottom edge of the front half such that said collar half is expandable radially for providing a greater minimum inner circumference to the front collar half by opening said slit, and
means for securing said body halves together with the end portions of said body halves in adjustable overlapping relation.

6. Emergency medical cervical collar according to claim 5 wherein said slit means extends through the smallest circumferential portion of the front half and permits the front half to expand radially to accommodate a neck having a circumference of up to approximately 23 inches when the slit means is opened.

7. Emergency medical cervical collar according to claim 5 wherein said front half is provided with a reinforcing laminate.

8. Emergency medical cervical collar according to claim 5 including an opening provided in said front collar half so as to provide access to the person's trachea, said slit extending from said opening to said front collar half bottom edge.

9. Emergency medical cervical collar according to claim 5 further comprising means for limiting expansion of said front collar half.

10. Emergency medical cervical collar according to claim 9 wherein said means for limiting expansion of said front collar half includes a strap fastener.

11. Emergency medical cervical collar comprising:
first and second discrete body halves,
one of said halves being a front half and the other being a rear half,
each half being generally U-shaped with a bight portion and a pair of end portions extending from the bight portion, and preformed from soft, flexible material, at least the rear half lacking reinforcing means which would prevent the rear half from being flexed to a substantially flattened position for slipping behind an accident victim's neck,
means for coupling said halves together with the end portions of said body halves in adjustable overlapping relation, and
means coupled to said rear collar half for adjustably encircling a portion of a person's head including the forehead to substantially prevent rotation or side-to-side movement of the head.

12. Emergency medical cervical collar according to claim 11 wherein the means for adjustably encircling the position of the person's head includes a strap fastener and a pad member slidable therealong, and said member having a friction surface for contacting a portion of the person's forehead whereby said strap fastener is substantially prevented from sliding on the person's forehead.

13. Emergency medical cervical collar according to claim 11 wherein said means for adjustably encircling a portion of the person's head includes a strap fastener and means for removably attaching said strap fastener to said rear collar half.

14. Emergency medical cervical collar according to claim 13 wherein said means for removably attaching said strap fastener includes fastener materials secured to said rear collar half.

15. Emergency medical cervical collar according to claim 11 wherein said rear collar half is provided with a rigid support member disposed along the bight portion thereof so as to permit flexing of the rear collar half to a substantially flattened position, said rigid member having a curved portion, and wherein said means for adjustably encircling a portion of the person's head is coupled to said support member curved portion at the bight portion of the rear collar half.

16. Emergency medical cervical collar according to claim 15 wherein said means for adjustably encircling the portion of the person's head is movably coupled to said support member curved portion so as to swivel thereon whereby said last-mentioned means may be moved to a cleared position so as to be readily accessible when said rear collar half is in position behind the person's head.

17. Emergency medical cervical collar according to claim 11 wherein said means for adjustably encircling a portion of the person's head is movably coupled to said rear collar half so as to swivel whereby said last-mentioned means may be moved to a cleared position so as to be readily accessible when said rear collar half is in position behind the person's head.

18. Emergency medical cervical collar according to claim 17 wherein said means for adjustably encircling a portion of the person's head includes a strap fastener coupled to said rear collar half so as to swivel thereon and means movably coupled to said rear collar half for guidably receiving said strap fastener.

19. Emergency medical cervical collar according to claim 18 wherein said means for guidably receiving said strap fastener includes a strap fastener guide member coupled to said rear collar half so as to swivel with respect thereto.

20. Emergency medical cervical collar according to claim 19 wherein said strap fastener guide member includes a swingable loop member for threading said strap fastener therethrough.

21. Emergency medical cervical collar comprising:
first and second discrete body halves,
one of said halves being a front half and the other being a rear half,
each half being generally U-shaped with a bight portion and a pair of end portions extending from the bight portion, and preformed from soft, flexible material, at least the rear half lacking reinforcing means which would prevent the rear half from being flexed to a substantially flattened position for slipping behind an accident victim's neck, and
means for drawing said body halves together such that said body halves self-align with the end portions of said body halves in adjustable overlapping relation, and for securely holding said body halves together as aligned.

22. Emergency medical cervical collar comprising:
first and second discrete body halves,
one of said body halves being a front half and the other being a rear half,
each half being generally U-shaped with a bight portion and a pair of end portions extending from the bight portion, and preformed from soft, flexible material, at least the rear half lacking reinforcing means which would prevent the rear half from being flexed to a substantially flattened position for slipping behind an accident victim's neck,
means for drawing said body halves together such that said body halves self-align with the end portions of said body halves in adjustable overlapping relation, and for securely holding said body halves together as aligned,
said front collar half having a chin support portion, the end portions of said front collar half extending from said chin support portion so as to enclose a substantial portion of the person's jawbone,
said rear collar half having a skull portion formed by said bight and end portions, the end portions of said rear collar half extending unitarily from said skull support portion sufficiently so as to overlap at least a portion of the person's ear, and
whereby said collar substantially prevents flexion, hyperextension and side-to-side movement of the person's head.

23. Emergency medical cervical collar according to claim 21 or claim 22 wherein said rear collar half is provided with one or more enlarged openings in the soft material for enabling said rear collar half to flex to a substantially flat shape.

24. Emergency medical cervical collar according to claim 21 or claim 22 including a rigid support member secured to said front collar half at the bight portion thereof, said support member and said front collar half having aligned openings for providing access to the person's trachea.

25. Emergency medical cervical collar according to claim 21 or claim 22 wherein said end portions of each body half extend from the bight portion thereof such that said overlapping relation between said end portions is adjustable to accommodate a range of adult neck sizes between approximately 11 inches and 18 inches.

26. Emergency medical cervical collar according to claim 21 or claim 22 wherein said end portions of each body half extend from the bight portion thereof such that said overlapping relation between said end portions is adjustable to accommodate a range of children's neck sizes between approximately 5 and 10 inches.

27. Emergency medical cervical collar according to claim 21 or claim 22 including means for adjustably encircling a portion of a person's head including the forehead to substantially prevent rotation or side-to-side movement of the head.

28. Emergency medical cervical collar according to claim 27 wherein said means for adjustably encircling the portion of the persons head is movably coupled to said rear collar half so as to swivel whereby said last-mentioned means may be moved to a cleared position so as to be readily accessible when said rear collar half is in a position behind the person's head.

29. Emergency medical cervical collar according to claim 27 wherein said means for adjustably encircling the portion of the person's head includes a strap fastener in a pad member slidable therealong, said pad member having a friction surface for contacting a portion of the person's forehead whereby said strap fastener is substantially prevented from sliding on the person's forehead.

30. Emergency medical cervical collar according to claim 29 wherein an end portion of said strap fastener is coupled to said rear collar half, said end portion comprising a fastener material, and wherein another portion of said strap fastener comprises a mating fastener material whereby said last-mentioned portion of said strap fastener may be secured by a releasable interlock to said end portion thereof.

31. Emergency medical cervical collar according to claim 21 or claim 22 wherein said rear collar half is provided with a rigid support member disposed along only the bight portion thereof so as to permit flexing of the rear collar half to a substantially flattened position, said rigid support member having a curved portion, and means coupled to said support member curved portion at the bight portion of the rear collar half for adjustably encircling a portion of the person's head including the forehead to substantially prevent rotation or side-to-side movement of the head.

32. Emergency medical cervical collar according to claim 31 wherein said means for adjustably encircling the portion of the person's head is movably coupled to said support member curved portion so as to swivel thereon whereby said last-mentioned means may be moved to a cleared position so as to be readily accessible when said rear collar half is in position behind the person's head.

33. Emergency medical cervical collar according to claim 31 wherein said means for adjustably encircling the portion of the person's head includes a strap fastener and a pad member slidable therealong, said pad member having a friction surface for contacting a portion of the person's forehead whereby said strap fastener is substantially prevented from sliding on the person's forehead.

34. Emergency medical cervical collar according to claim 33 wherein an end portion of said strap fastener is coupled to said rear collar half, said end portion comprising a fastener material, and wherein another portion of said strap fastener comprises a mating fastener material whereby said last-mentioned portion of said strap fastener may be secured by a releasable interlock to said end portion thereof.

35. Emergency medical cervical collar according to claim 21 or claim 22 wherein said means for adjustably drawing said body halves together such that said body half self-align, and for holding said body halves together as aligned, includes a strap fastener coupled to said rear collar half and means movably coupled to said front collar half for guidably receiving said strap fastener, said lastmentioned means being movable to a position whereby said collar halves self-align as said strap fastener is drawn therethrough.

36. Emergency medical cervical collar according to claim 35 wherein each of the end portions of strap fastener comprises a fastener material and wherein a portion of the strap fastener between said end portion is provided with a mating fastener material whereby each end portion of the strap fastener may be folded back and secured to said portion of the strap fastener therebetween.

37. Emergency medical cervical collar according to claim 35 wherein said means for guidably receiving such strap fastener includes a pair of strap fastener guide members coupled to said front collar half so as to swivel with respect thereto.

38. Emergency medical cervical collar according to claim 37 wherein each strap fastener guide member includes a swingable loop member for threading said strap fastener therethrough.

39. Emergency medical cervical collar according to claim 21 or claim 22 wherein said drawing means further comprises:
   a rigid reinforcement support member fixed adjacent a bight portion of said front collar half and including a slot through each lateral edge portion thereof.

40. Emergency medical cervical collar according to claim 39 further comprising:
   a strap fastener guide anchored to said front collar half and passing through said slot.

41. Emergency medical cervical collar according to claim 39 further comprising:
   a strap fastener affixed to said support member through said slot.

42. Emergency medical cervical collar according to claim 41 further comprising:
   a rigid reinforcement support member affixed adjacent to a bight portion of said rear collar half and including a pair of strap fastener guides anchored thereto.

43. Emergency medical cervical collar according to claim 21 or claim 22 or claim 11 wherein said body halves are water resistant.

44. Emergency medical cervical collar according to claim 43 wherein said body halves are sufficiently buoyant to float in water.

* * * * *